(12) United States Patent
Landowski et al.

(10) Patent No.: US 8,844,942 B1
(45) Date of Patent: Sep. 30, 2014

(54) QUICK-LOAD CONNECTOR FOR A SURGICAL TOOL

(75) Inventors: Steve Landowski, Paddock Lake, WI (US); Kevin K. Marchant, Sturtevant, WI (US)

(73) Assignee: Greatbatch Ltd., Clarence, NY (US)

( * ) Notice: Subject to any disclaimer, the term of this patent is extended or adjusted under 35 U.S.C. 154(b) by 298 days.

(21) Appl. No.: 13/169,742

(22) Filed: Jun. 27, 2011

Related U.S. Application Data

(60) Provisional application No. 61/358,441, filed on Jun. 25, 2010.

(51) Int. Cl.
*B23B 31/107* (2006.01)
*B23B 31/22* (2006.01)

(52) U.S. Cl.
USPC .................. 279/75; 279/22; 279/30; 279/905

(58) Field of Classification Search
USPC ........ 279/75, 905, 22, 82, 74, 30, 904, 80, 29
See application file for complete search history.

(56) References Cited

U.S. PATENT DOCUMENTS

| | | | |
|---|---|---|---|
| 4,403,959 A | 9/1983 | Hatakeyama | |
| 4,616,635 A | 10/1986 | Caspar et al. | |
| 5,398,946 A * | 3/1995 | Quiring | 279/30 |
| 5,505,737 A | 4/1996 | Gosselin et al. | |
| 5,630,832 A | 5/1997 | Giordano et al. | |
| 5,928,241 A * | 7/1999 | Menut et al. | 606/80 |
| 5,954,347 A * | 9/1999 | Buck et al. | 279/20 |
| 6,045,564 A | 4/2000 | Walen | |
| 6,457,916 B2 * | 10/2002 | Wienhold | 408/240 |
| 6,561,523 B1 * | 5/2003 | Wienhold | 279/30 |
| 7,448,302 B2 * | 11/2008 | Huang | 81/438 |
| 7,600,451 B2 | 10/2009 | Lechot et al. | |
| 7,740,249 B1 * | 6/2010 | Gao | 279/75 |
| 7,810,817 B1 * | 10/2010 | Gao | 279/75 |
| 2005/0116429 A1 * | 6/2005 | Chang | 279/75 |
| 2008/0243133 A1 | 10/2008 | Heinz | |
| 2010/0207335 A1 * | 8/2010 | Lin | 279/22 |
| 2012/0326400 A1 * | 12/2012 | Lin | 279/75 |

FOREIGN PATENT DOCUMENTS

| | | |
|---|---|---|
| DE | 3509787 | 10/1985 |
| EP | 0888751 A2 | 1/1999 |
| JP | 61041445 | 2/1986 |
| WO | 9105514 | 5/1991 |

* cited by examiner

*Primary Examiner* — Eric A Gates
*Assistant Examiner* — Paul M Janeski
(74) *Attorney, Agent, or Firm* — Michael F. Scalise

(57) ABSTRACT

A mechanical connector designed to connect an orthopedic tool to a handle or motor. The connector includes a locking ball and spring-load sleeve mechanism that compresses a ball into an annular groove of the tool drive shaft, locking the shaft in the connector. The tool drive shaft is released from the connector by applying a force to the housing in a proximal direction. A portion of the housing removes the locking ball from the groove of the tool drive shaft, unlocking the shaft from the connector as the housing travels in a proximal direction.

20 Claims, 8 Drawing Sheets

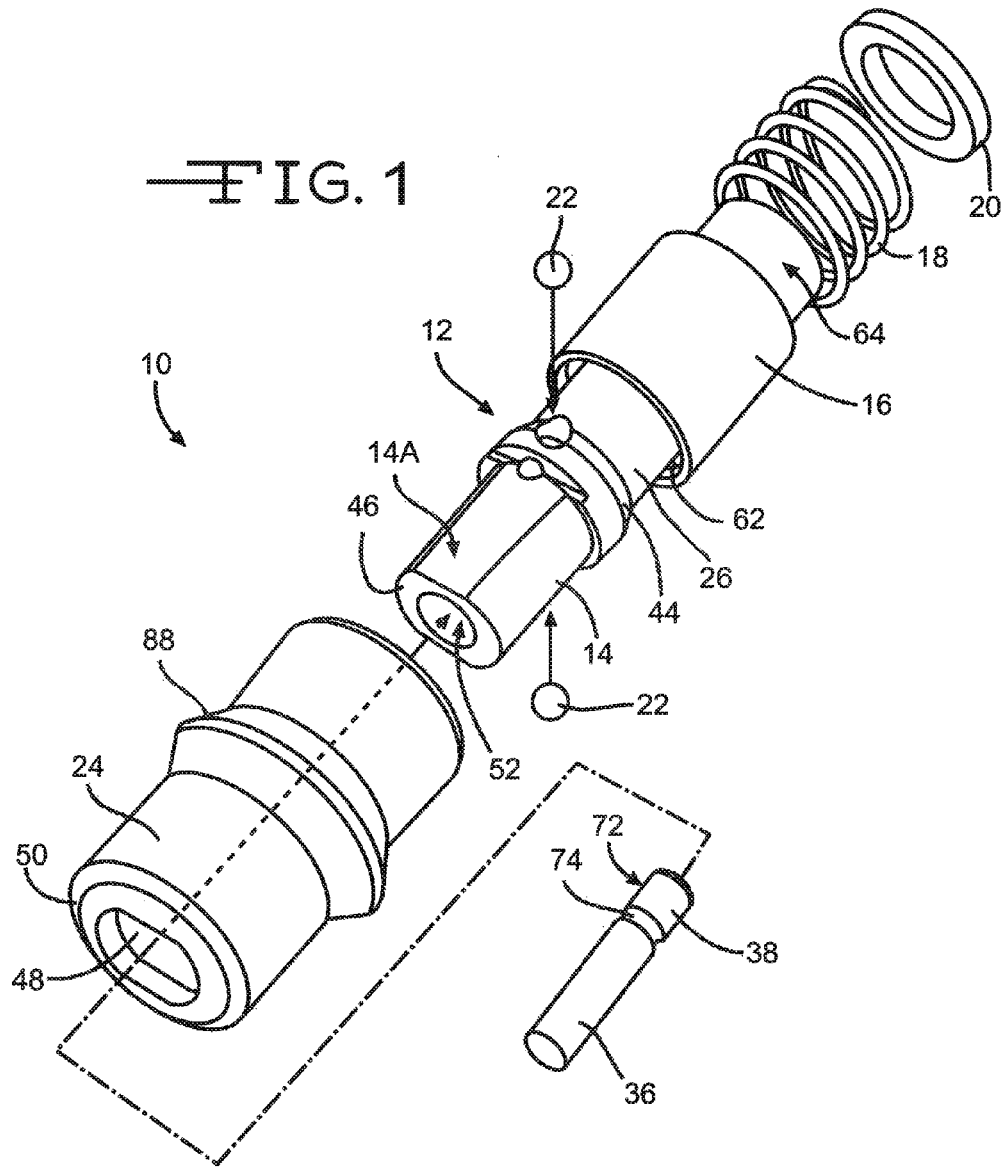

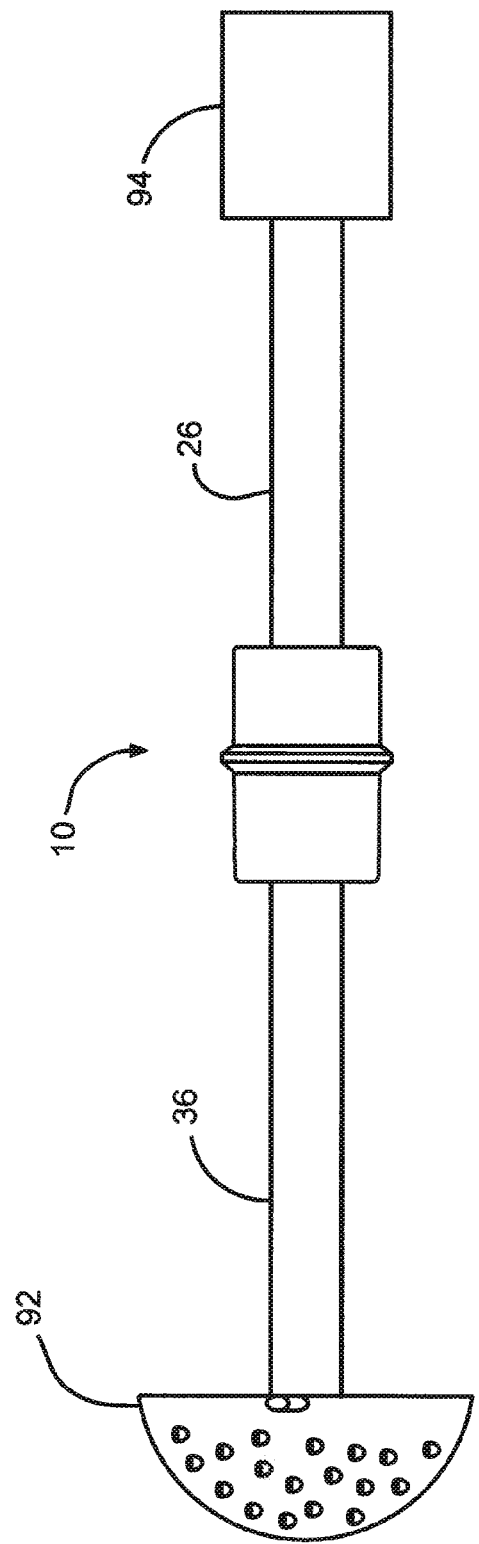

QUICK-LOAD CONNECTOR FOR A SURGICAL TOOL

CROSS-REFERENCE TO RELATED APPLICATIONS

This application claims priority from U.S. Provisional Patent Application Ser. No. 61/358,441 filed Jun. 25, 2010.

BACKGROUND OF THE INVENTION

1. Field of the Invention

The present invention relates generally to surgical instruments for use in orthopedic tools. In particular, the present invention relates to a connector for securing an orthopedic tool to a drive device.

2. Prior Art

Surgical tools for use in the cutting of bone and tissue are conventional in the art. Many of these tools are connected to a handle or motor, which is used to manipulate and drive the tool during a surgical procedure.

Generally, these tools are used to cut and shape bone as well as remove tissue in preparation for insertion of an orthopedic implant. As such, these procedures require that bone and/or tissue be precisely cut and/or removed to ensure proper positioning and fit of an orthopedic implant. Any unexpected movement of the surgical tool during use, such as handle slippage, unintentional rotation, or mechanical play, is not optimal as it could result in undesirable surgical outcomes.

Many prior art tool connectors are prone to these problems. For example, some prior art connectors are designed such that they contact a smooth outer diameter of the shaft of the tool. The contacting portion of a connector of such a prior art design could move along the tool shaft during use, resulting in unexpected slippage of the tool within its handle.

Additionally, some prior connector devices require that the locking mechanism be activated before insertion of the tool shaft. This limitation requires an additional step in connecting the tool to a handle during the surgical procedure. Activation of the locking mechanism may require assistance which may not be available when required. Furthermore, the orientation of such a connector activation mechanism may not be ideally positioned during the surgical procedure. For example, a button or lever mechanism may be oriented in a position that is difficult to reach or is not accessible. Unlike these prior art devices, a tool drive shaft is simply inserted and advanced into the connector of the present invention where it is locked into place. This locking feature of the connector of the present invention provides an efficient and secure means by which a tool is connected to a drive device, such as a handle or motor.

Therefore, for these reasons, it is desirable to provide a mechanical connector with an improved locking mechanism. A connector locking mechanism that offers a more secure, robust, easy to use, efficient connection between an orthopedic tool and drive device is provided by the present invention.

The connector of the present invention comprises a ball and a spring-loaded sleeve mechanism, which engages a groove that circumferentially extends around the drive shaft of a tool. The tool drive shaft is locked into place by a series of locking balls, which are forced into an annular groove of the drive shaft by the spring-loaded sleeve. The mechanism of the present invention is designed such that when in the locked position, forward and rearward movement of the tool drive shaft is prevented by an interference relationship of the balls captured between the spring-loaded sleeve and the annular groove of the tool drive shaft.

Additionally, the connector mechanism of the present invention accommodates drive shafts of differing size diameters. The spring-loaded sleeve, located within the mechanism, enables the balls to lock with shafts of differing diameters, both large and small. Also, the spring action of the sleeve mechanism of the present invention allows for the locking balls to contact drive shafts of different diameters. This enables an operator to robustly secure tool drive shafts with diameter tolerance variations. Furthermore, the design of the present connector mechanism does not require special tool shaft designs. Existing tool drive shafts can easily be inserted and locked into the connector of the present invention.

The features of the locking mechanism of the connector of the present invention address the shortcomings of prior locking connectors. The present connector provides a more reliable and selectively releasable connection between the surgical tool and its handle or motor, thereby reducing undesired mechanical movement such as mechanical play, slippage and/or unintentional rotation between the tool drive shaft and the handle or motor. These features and other benefits will be further discussed with respect to the locking connector of the present invention described herein.

SUMMARY OF THE INVENTION

The present invention provides a mechanical connector by which a tool drive shaft is connected, or coupled, and releasibly secured to a drive device. The tool drive shaft may comprise the shaft of an orthopedic tool such as a reamer, a bone cutter, a retractor, a saw, a drill, or the like. The drive device may comprise a handle, a motor or another drive shaft.

The present connector comprises a locking mechanism sub-assembly positioned circumferentially around an elongated cylindrically shaped body. A connector housing encloses the locking mechanism therewithin. The distal and proximal ends of the cylinder extend through their respective ends of the connector housing.

A through-bore, extending along a central longitudinal axis of the body, is dimensioned to receive a drive shaft. The locking mechanism sub-assembly comprises a spring-loaded sleeve and a series of locking balls. Each of the locking balls is individually received in respective slots that extend through a wall of the body. The spring-loaded sleeve is positioned circumferentially over the body such that the sleeve is in an axially manipulatable relationship along the longitudinal axis of the body. A spring, positioned proximal of the sleeve, exerts a biasing force that is selectively manipulatable to retain the locking balls within their respective slot of the body. In the locked position, a portion of each ball protrudes through its slot into the through-bore opening of the body. It is this portion of the ball that interfaces with the annular groove of the tool drive shaft to thereby secure the tool within the connector.

The "quick-load" aspect of the connector of the present invention allows the tool drive shaft to be quickly inserted and secured to a handle drive device by simply advancing the drive shaft into the connector. Once secured in the connector, the tool drive shaft cannot be removed from the handle until the collar is pulled in a backwards or distal direction, away from the tool drive shaft located within the connector. Alternatively, the tool drive shaft could also be removed by advancing a distal end portion of the connector body in a proximal direction into the connector.

When the tool drive shaft is inserted into the present connector, the outer surface of the tool drive shaft forces the locking balls upwardly or laterally into the body slot and away from the drive shaft. The drive shaft is further advanced into the body of the connector until its annular groove is aligned with the cylinder slot. Once the drive shaft groove and cylinder slot are aligned, the ball residing within the slot is captured in the groove of the tool drive shaft by the spring-loaded sleeve, thereby locking the tool to the connector.

The spring-loaded sleeve, located within the body of the present connector provides a sufficient amount of tension to the balls in the groove of the drive shaft, thereby locking the drive shaft within the connector. An angled interior wall of the cylinder slot prevents release movement of the tool drive shaft from the connector. That is because the locking balls are incapable of advancing past the interior cylinder wall. Likewise, rearward movement of the drive shaft is impeded by an interior wall surface of the housing.

The drive shaft is released from the connector by pulling the collar housing in a proximal direction, away from the distal end of the tool drive shaft. This action causes a lip of the collar housing to contact the locking balls and move them in an upwardly or lateral direction out of the tool groove, thereby freeing the tool drive shaft from the interference fit with the locking balls. In an alternative embodiment, the tool drive shaft can be removed by pushing the distal end portion of the connector body, either the nozzle portion or the cylinder portion, proximally into the connector. This alternate action causes an edge located at a proximal end of the nozzle or distal portion of the cylinder, to contact the locking balls and move them in an upwardly or lateral direction out of the tool groove. Once the balls have been removed from the annular groove of the tool drive shaft, the tool can be removed from the connector.

These and other objects and advantages of the present invention will become increasingly more apparent by a reading of the following description in conjunction with the appended drawings.

DESCRIPTION OF THE DRAWINGS

FIG. 1 is an exploded perspective view of the connector mechanism of the present invention.

FIG. 9B is a side view illustrating the present connector connected to an orthopedic tool and a motor.

DETAILED DESCRIPTION OF THE INVENTION

Figure 1A:
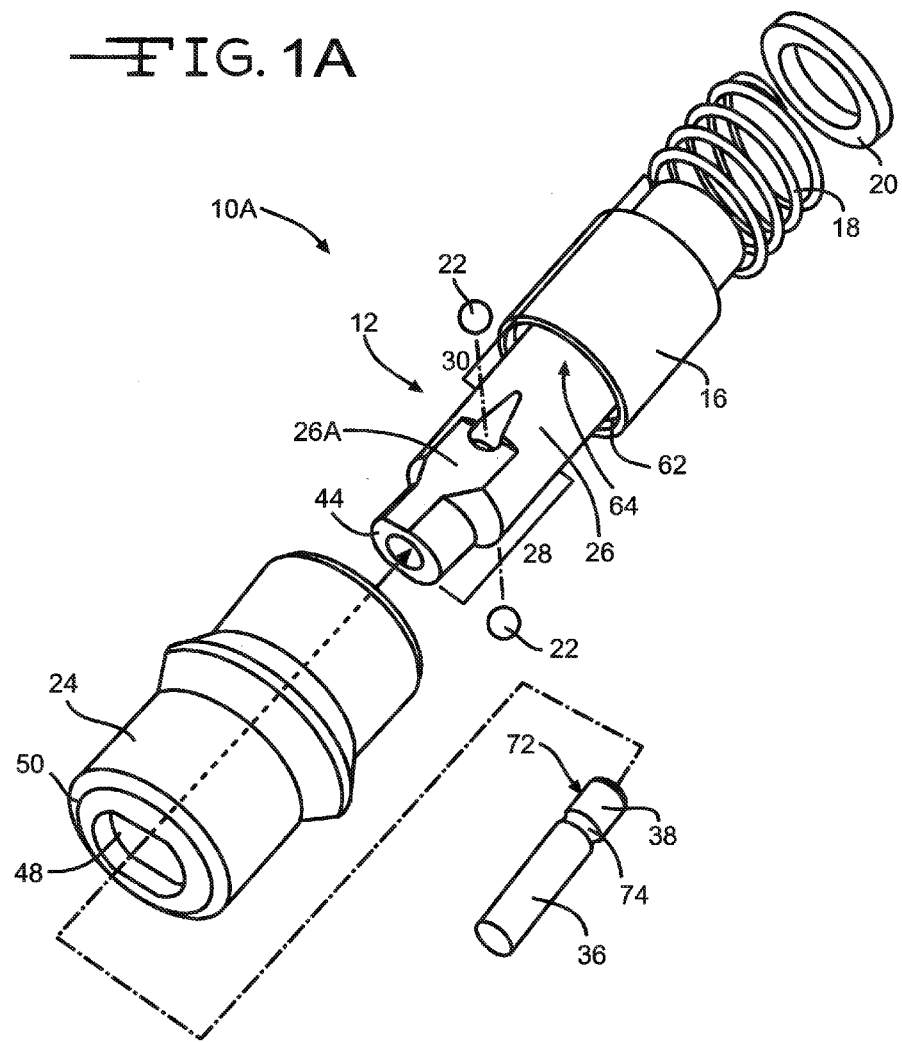
FIG. 1A is an exploded perspective view of an alternate embodiment of the present connector.

Referring now to the figures, FIGS. 1-9B illustrate embodiments of the connector mechanism 10 of the present invention. As illustrated in FIG. 1, the connector 10 comprises an elongated cylindrically shaped body 12, a nozzle portion 14 of the body, a sleeve 16 positioned circumferentially around the body 12, a spring 18, a bushing 20, and at least one locking ball 22. A collar 24 serves as a housing for the present connector 10.

In a preferred embodiment, the body 12 comprises a proximal cylindrical portion and a distal cylindrical portion with a planar portion 26A of a reduced outer diameter (FIG. 1A). More preferably, the body 12 comprises a distal cylindrically shaped nozzle 14 connected to a proximal main cylinder 26 of an increased diameter. The cylindrically shaped nozzle 14 also comprises a planar portion 14A along its outer diameter (FIG. 1).

The main cylinder 26 has a length extending between a cylinder distal end portion 28, and a cylinder proximal end portion 30. In a more preferred embodiment, the main cylinder 26 is constructed with a through-bore 32 that extends along a central longitudinal axis A-A thereof. A cylinder wall 34 surrounds the through-bore 32 and extends along the longitudinal axis A-A. The cylinder through-bore 32 of the main cylinder 26 is dimensioned to receive a tool drive shaft 36, more preferably a distal end portion 38 of the tool drive shaft 36. In a preferred embodiment, the main cylinder 26 has a diameter from about 0.5 cm to about 5.0 cm, with the through-bore 32 preferably having a diameter from about 0.3 cm to about 3.0 cm.

In a preferred embodiment, as shown in FIGS. 1, and 2-8, the housing 24 is positioned over the connector 10 such that it encloses the connector 10 therewithin. The body 12 comprises a distal cylindrically-shaped nozzle 14 connected to a proximal, main cylinder 26 of an increased outer diameter. The nozzle 14 extends from a nozzle distal end portion 40 to a nozzle proximal end portion 42 and is fluidly connected to a distal end 28 of the main cylinder 26. A distal end 46 of the nozzle 14 protrudes through an opening 48 at the distal end 50 of the connector housing 24. The nozzle 14 is attached to the main cylinder 26 such that a nozzle through-bore 52 is coaxial with the longitudinal axis A-A of the main cylinder 26. A slot 54 is provided through a wall 56 of the nozzle 14 and delineates the proximal nozzle portion 42 from the main cylinder 26.

In an equally preferred embodiment, shown in FIG. 1A, the connector 10A can be constructed without the nozzle 14 and the main cylinder 26 being separate parts. In this preferred embodiment, the cylinder 26 is elongated such that its distal end 44 protrudes through the distal opening 48 of the connector housing 24.

The slot 54 may reside where the cylindrical body portions 14, 26 meet each other (FIG. 1). The slot 54 may be positioned through the wall 34 of the cylinder 26 (FIG. 1A) or through the wall 56 of the nozzle 14. More preferably, the slot 54, may be positioned within the distal end portion 28 of the cylinder 26. Whether positioned through the nozzle 14 and/or cylinder 26, it is preferred that at least two slots 54 extend through their respective wall thicknesses that comprise the body 12 of the present connector 10, 10A.

Figure 9A:
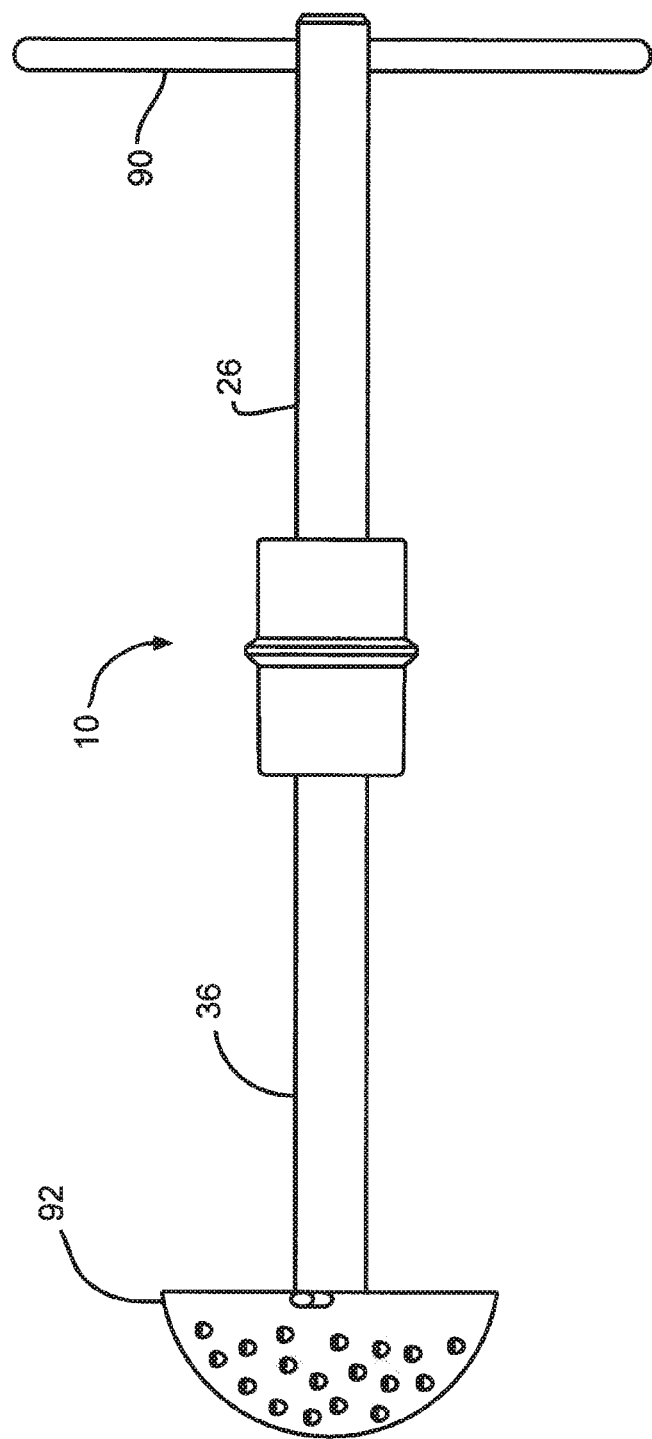
FIG. 9A is a side view illustrating the present connector connected to an orthopedic tool and a handle.

An orthopedic tool 92, including but not limited to a reamer, a bone cutter, a saw, a retractor, a drill, and the like, is releasably connectable or couplable to the distal end portion 28, 40 of the cylinder 26 or nozzle 14 comprising the connector 10, 10A. A handle 90 or a motor 94 preferably connects to the proximal end portion 30 of the cylinder 26. However, it is contemplated that the tool 92 or the handle 90 or the motor 94 could be attached to their respective opposite ends of the connector 10, 10A. Non-limiting examples of the connector 10, 10A of the present invention are illustrated in FIGS. 9A and 9B showing the connector 10, 10A connected to an orthopedic tool 92 and a handle 90 (FIG. 9A) as well as an orthopedic tool 92 and a motor 94 (FIG. 9B).

The sleeve 16, having a length extending from a sleeve distal end 58 to a sleeve proximal end 60, is preferably positioned over the proximal end portion 30 of the main cylinder 26. Specifically, the sleeve 16 has a sleeve through-bore 62 through which the cylinder 26 resides. The sleeve 16 is preferably mounted in, an axially manipulatable relationship over the main cylinder 26. In other words, the sleeve 16 is positioned in an axial slidable relationship over an outer surface 64 of the main cylinder 26 in a co-axial relationship with the longitudinal axis A-A.

Figure 2:
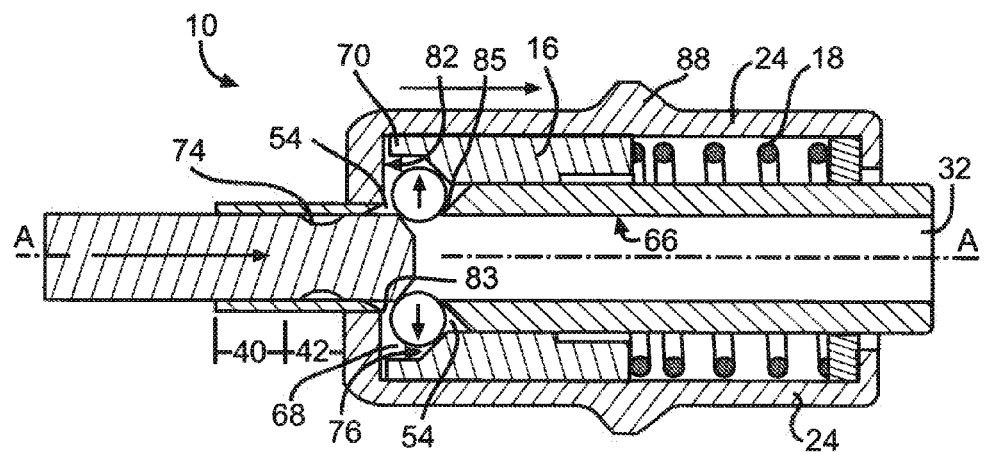
FIG. 2 is a cross-sectional view of the connector mechanism of the present invention during initial insertion of a tool drive shaft.
Figure 3:
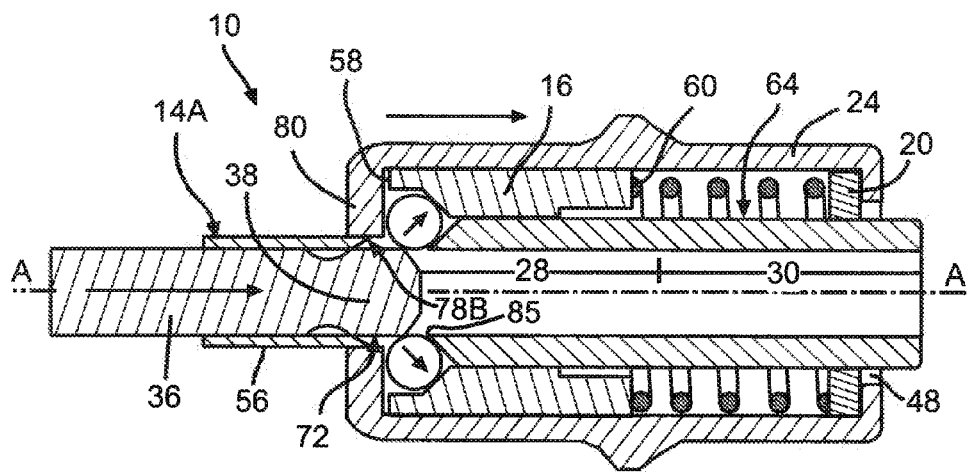
FIG. 3 is a cross-sectional view of the present connector during insertion of the tool drive shaft.
Figure 4:
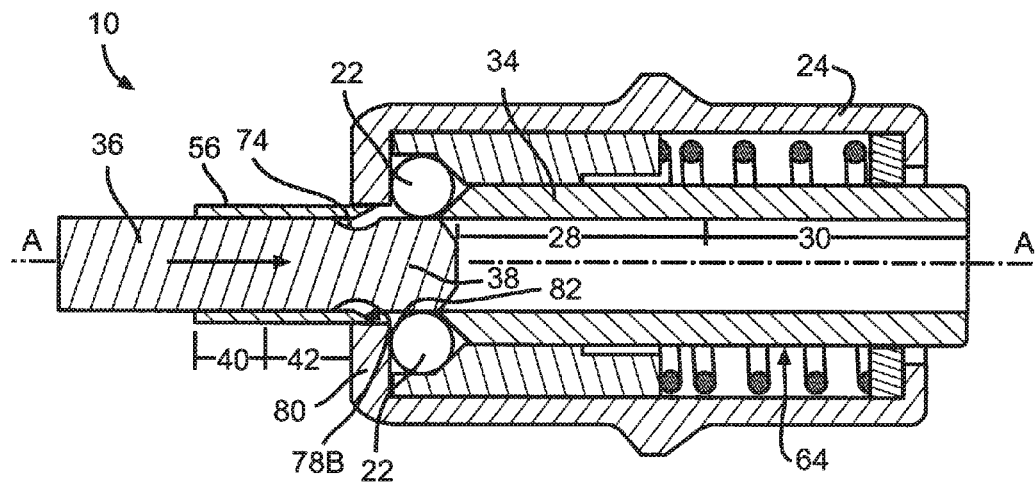
FIG. 4 is a cross-sectional view of the present connector locking mechanism illustrating further insertion of the tool drive shaft.

In a preferred embodiment, the spring 18 is positioned over the proximal end portion 30 of the main cylinder 26. The spring 18 is further positioned such that its proximal end contacts the proximal end 60 of the sleeve 16. The bushing 20 is positioned over the proximal end 30 of the cylinder 26 and contacts the other end of the spring 18. The spring 18 therefore, resides between the sleeve 16 and the bushing 20. The bushing 20 acts as a "back stop" preventing the spring 18 from moving in a distal direction along the main cylinder 26. As illustrated, the proximal end of the spring 18 contacts the stationary bushing 20 as its biasing force is changed by forward or distal and rearward or proximal movement of the sleeve 16 within the housing 24. As shown in FIGS. 2-4, the spring 18 provides tension that normally forces the sleeve 16 distally within the connector housing 24.

The locking ball 22 is received within the slot 54 that extends through the wall of the body 12 where the distal cylindrical portion 28 meets the proximal nozzle portion 42 (FIGS. 1). A portion of the ball 22 protrudes below an inner wall surface 66 of the body 12. In a more preferred embodiment, there are at least two balls 22 positioned opposite each other within the present connector 10, as shown in FIGS. 2-8. Although two balls 22 are preferred, it is contemplated that additional balls 22 could be positioned circumferentially around the cylinder 26 or nozzle 14 within the connector 10, 10A.

In use, when the distal end portion 38 of a tool drive shaft 36 is introduced into the through-bore 32, 52 of the body 12, as shown in FIG. 3, the drive shaft 36 forces the ball or balls 22 outwardly and latterly along the slot 54. As such, the ball 22 retreats within the slot 54, pushing against the distal end 58 of the sleeve 16, thus forcing the sleeve 16 against the spring 18. As shown in FIGS. 2-8, the distal end 58 of the sleeve 16 is preferably designed with a cutout portion 68. This cutout portion 68 has a frusto-conical shape that extends outwardly and distally from an inner surface 76 of the sleeve 16 part-way through a thickness thereof at an angle of from about 35° to about 55° with respect to the longitudinal axis A-A, where it meets a cylindrical ledge 70 extending to the distal end 58 of the sleeve 16. The cutout 68 is designed to allow a portion of the ball 22 to reside therein.

As the distal end 38 of the drive shaft 36, is advanced further into the through-bore 32, as illustrated in FIG. 4, the ball 22 rides along the outer surface 72 of the drive shaft 36. The distal end portion 38 of the shaft 36 is further advanced until its annular groove 74 is aligned with the slot opening 54 provided in the body 12 where the ball 22 resides. Once aligned, the ball 22, within the slot 54, falls into the annular groove 74 of the tool drive shaft 36. The angled distal edge 76 of the sleeve 16 in combination with the spring 18, imparts a downward force onto the ball 22, locking the shaft 36 therewithin. In a preferred embodiment, about 10 percent to about 45 percent of the diameter of the ball 22 resides within the annular groove 74 of the drive shaft 36 when in the locked position.

The spring-loaded sleeve 16 and ball 22 feature of the present connector 10, 10A prevent both forward and rearward (proximal and distal) movement of the tool drive shaft 36. Forward or proximal movement of the tool 92 is prohibited because such movement forces the ball 22 against an interior wall surface 78A of the slot 54. Specifically, the interior wall surface 78A of the slot 54 is angled such that the ball 22 cannot move out of the groove 74. In a preferred embodiment, the interior wall surface 78A of each slot 54 is at an angle ranging from about 35' to about and more preferably at about 45° with respect to the longitudinal axis A-A. Similarly, rearward or distal movement of the drive shaft 36 is prohibited by an annular lip 80 of the housing 24. As shown in FIGS. 2-5, the lip 80 is oriented at a normal relationship with respect to the longitudinal axis A-A.

Figure 5:
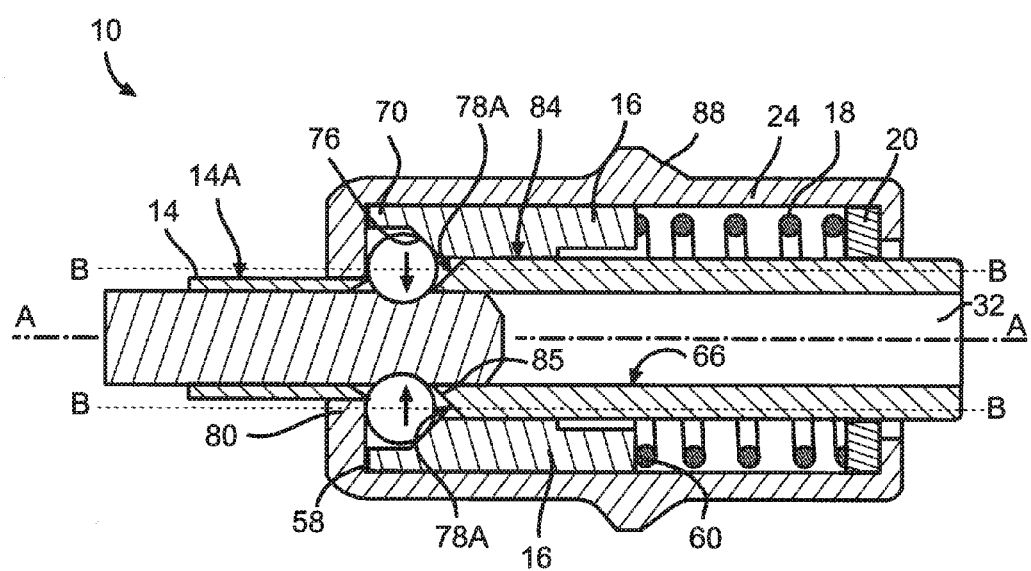
FIG. 5 is a cross-sectional view illustrating a locked tool drive shaft in the connector mechanism of the present invention.

Furthermore, as illustrated in FIG. 5, when in the locked position, a centerline BB of the ball 22 is positioned below the outer surface 84 of the proximal cylindrical portion 28, of the body 12, thus preventing the ball 22 from becoming dislodged from its position within the annular groove 74 of the tool shaft 36. These preferred features of the connector 10, 10A of the present invention prevent further unintentional movement of the tool drive shaft 36.

Figure 6:
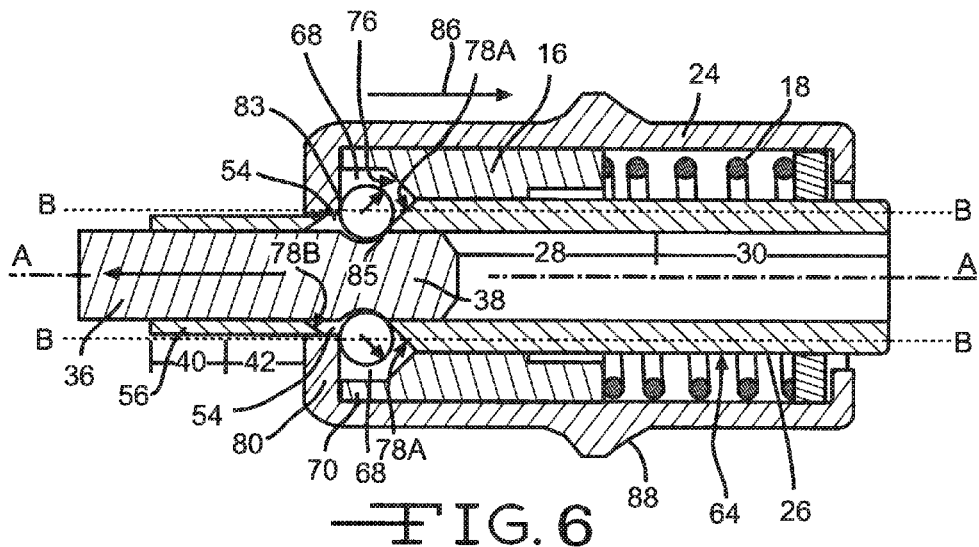
FIG. 6 is a cross-sectional view illustrating the tool drive shaft beginning to be released from the connector mechanism of the present invention.
Figure 7:
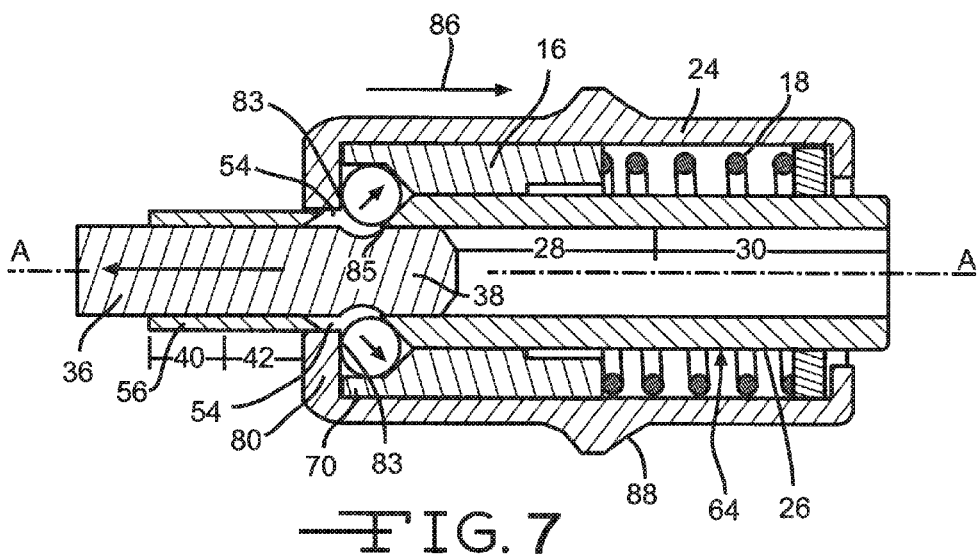
FIG. 7 is a cross-sectional view illustrating the locking balls removed from the annular groove of the drive shaft.

In a preferred embodiment, the drive shaft 36 is removed from the connector 10, 10A by applying a force the housing 24 in a proximal direction as indicated by arrow 86 towards the proximal end 30 of the cylinder 26 (FIGS. 6 and 7). As this force is applied, the interior wall surface 82 of the housing 24 contacts the ball 22 and the distal edge 58 of the sleeve 16 as it moves in a proximal direction toward the proximal end 30 of the cylinder 26. A ridge 88, circumferentially surrounding the collar housing 24 provides a raised surface by which the user can manipulate the collar in both a forwardly or distal and a rearwardly or proximal direction.

As the housing 24 is moved proximally along the cylinder 26 and/or nozzle 14, the annular lip 80 of the connector housing 24 contacts the ball 22. As the lip 80 continues in a proximal direction, the ball 22 is pushed up the angled interior surface 78A of the slot 54. The cutout portion 68 of the sleeve 16 allows space for the ball 22 to roll therewithin. Furthermore, the interior surface 78A of the slot 54 acts as a ramp surface, which allows the ball 22 to roll out of the annular groove 74 of the tool shaft 36. As shown in FIGS. 6 and 7, edge 85 of the interior surface 78A, acts similarly to a scoop in that it works in concert with annular lip 80 to pick the ball 22 out of the groove 74. Once the ball 22 is removed from the groove 74, the shaft 36 can be removed from the connector 10, 10A.

When in the locked position shown in FIG. 5, the centerline B-B of the ball 22 is spaced at or above the cylindrical outer surface 14A of the nozzle portion 14 or the distal cylindrical portion 26A of the connector 10A shown in FIG. 1A. This relative positioning enables the annular lip 80 of the housing 24 to contact the ball 22 to initiate movement of the ball 22 in an upwardly and lateral direction out of the annular groove 74 in the tool drive shaft 36 as shown in FIG. 6. In a preferred embodiment, the applied force causes the housing 24 to contact the sleeve 16 to move the sleeve in a proximal direction, which compresses the spring 18 against the bushing 20.

As the housing 24 and its annular lip 80 are moved in a proximal direction, it is noted that an edge 83 of the lip 80 is either aligned along the center line BB of the ball 22 or somewhat spaced toward the tool drive shaft with respect to the axis B-B. This relative positioning causes the edge 83 of the lip 80 to "pick" the ball 22 out of the annular groove 74 in the tool drive shaft 36 and push it out and up surface 78A. In addition, edge 85 of surface 78A together with edge 83 impart a "scooping" action onto ball 22 that pushes up surface 78A and out of groove 74.

In a preferred embodiment, edge 85 of the interior surface 78A of slot 54, resides below the centerline B-B of the ball 22. In this preferred embodiment, the position of edge 85 of the angled interior surface 78A imparts a "scooping" action below the equator of the ball 22 which helps lift the ball out of the groove 74.

Figure 8:
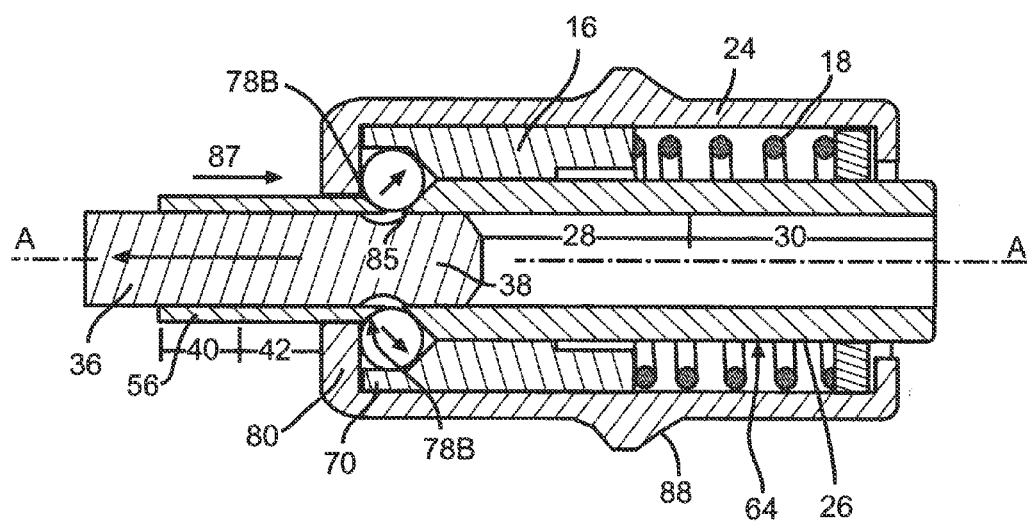
FIG. 8 is a cross-sectional view illustrating an alternate embodiment of the locking balls being removed from the annular groove of the drive shaft.

In an alternate embodiment shown in FIG. 8, the connector 10, 10A of the present invention could be designed such that it is released through proximal movement of the distal end portion of the body 12. In this alternate embodiment, the proximal portion 28, 42 of the distal end portion of the connector 10, 10A is slid between lip 80 and surface 72 of the drive shaft 36 while the housing 24 is in a stationary position.

As shown in FIG. 8, surface 78B is a mirror image of surface 78A. Surface 78B, like surface 78A, is angled from about 35° to about 55° degrees with respect to longitudinal axis A-A. Similarly to surface 78A, surface 78B acts as a ramp surface that "picks" ball 22 out of groove 74 of the tool drive shaft. As surface 78B moves in a proximal direction it preferably contacts the ball 22 below centerline B-B, pushing it out of the groove, onto surface 78A and out of groove 74. This action further compresses spring 18 as the ball 22 contacts surface 76 of sleeve 16 within the housing 24.

It is contemplated that surface 78B is non-limiting and could comprise the proximal end of the nozzle 14 or a distal portion 28 of the cylinder 26. Furthermore, it is contemplated that surface 78B could comprise the proximal end of a sleeve or tube that is positioned over the distal end portion of the body 12.

It is appreciated that various modifications to the invention concepts described herein may be apparent to those of ordinary skill in the art without departing from the scope of the present invention as defined by the appended claims.

What is claimed is:

1. A connector mechanism for a surgical tool, the mechanism comprising:
   a) a housing comprising a housing sidewall surrounding a housing through-bore extending along a longitudinal axis from a housing proximal portion defining a housing proximal open end to a housing distal portion having a lip aligned substantially perpendicular to the axis and defining a housing distal open end;
   b) a connector residing inside the housing through-bore, wherein the connector comprises a connector sidewall having a connector sidewall thickness surrounding a connector through-bore sized to receive a tool shaft, wherein the connector through-bore extends along the longitudinal axis from a connector proximal portion having a connector proximal open end to a connector distal portion having a connector distal open end;
   c) at least one slot extending through the connector sidewall from an outer connector surface to the connector through-bore thereof, wherein the slot has an angled surface extending from the connector inner surface proximally and outwardly with respect to the longitudinal axis through the connector sidewall thickness;
   d) a sleeve positioned between the housing and the connector, the sleeve comprising a sleeve sidewall having a sleeve thickness extending from a sleeve outer surface to a sleeve inner surface defining a sleeve through-bore extending along the longitudinal axis from a sleeve proximal portion having a sleeve proximal open end to a sleeve distal portion having a sleeve distal open end, wherein the sleeve is supported on an outer surface of the connector sidewall in an axially movable relationship therewith and wherein the sleeve distal portion has a cut-out comprising a frusto-conically shaped surface extending distally and outwardly with respect to the longitudinal axis from the sleeve inner surface at least part-way through the sleeve thickness to the sleeve distal open end;
   e) a spring positioned circumferentially around the connector within the housing, wherein the spring biases between the housing proximal portion and the sleeve proximal portion; and
   f) at least one locking ball received within the at least one slot, the ball being sized to extend only part-way into the connector through-bore from the slot,
   g) wherein proximal axial movement of a tool shaft into the connector through-bore causes the at least one ball to move proximally and outwardly along the angled surface of the connector slot and into the sleeve cut-out as the biased sleeve moves proximally along the connector until the ball is laterally removed from the connector through-bore so that the tool shaft is receivable therein, and
   h) wherein when an annular groove in the tool shaft is aligned with the ball, the biased sleeve moves in a distal direction, which causes the ball to move laterally into the tool shaft groove until the ball is captured therein by the connector slot and against the frusto-conical surface of the sleeve cut-out and the distal lip of the housing, and
   i) wherein the housing is then manipulatable in a proximal direction to cause the lip to contact the ball and the distal sleeve end to thereby cause the ball to move along the angled surface of the connector slot as the housing simultaneously moves the biased sleeve proximally with the ball again moving along the frusto-conical surface of the sleeve cut-out to thereby laterally remove the ball from the tool shaft groove so that the tool shaft is manipulatable in a distal direction out of the connector through-bore.

2. The connector mechanism of claim 1 wherein the connector comprises a nozzle connected to a cylinder, the nozzle residing at the distal end of the cylinder.

3. The connector mechanism of claim 2 wherein the nozzle is connected to the cylinder such that a nozzle through-bore is a portion of the connector through-bore along the longitudinal axis.

4. The connector mechanism of claim 2 wherein the slot extending through the connector sidewall resides where the nozzle and cylinder connect.

5. The connector mechanism of claim 1 wherein the angled surface of the slot is angled from about 35° to about 55° with respect to the longitudinal axis of the connector.

6. The connector mechanism of claim 1 wherein, with the ball received in the groove of the tool shaft, an edge of the connector sidewall an interior surface at the slot is positioned below a centerline of the locking ball.

7. The connector mechanism of claim 1 wherein the housing has a ridge that protrudes from an outer housing surface and extends circumferentially around the housing.

8. The connector mechanism of claim 1 wherein the proximal portion of the connector is removably connectable to a surgical tool handle or a motor.

9. The connector mechanism of claim 1 being removably connectable to an orthopedic tool comprising the tool shaft.

10. The connector mechanism of claim 1 wherein, with respect to the longitudinal axis, the connector proximal portion protrudes axially beyond the housing proximal open end and the connector distal portion protrudes axially beyond the housing distal open end.

11. The connector mechanism of claim 1 wherein the lip at the distal housing portion is an annular lip.

12. A connector mechanism for a surgical tool, the mechanism comprising:
   a) a housing comprising a housing sidewall surrounding a housing through-bore extending along a longitudinal axis from a housing proximal portion defining a housing proximal open end to a housing distal portion, having an annular lip aligned substantially perpendicular to the axis and defining a housing distal open end;
   b) a connector residing inside the housing through-bore, wherein the connector comprises a connector sidewall having a connector sidewall thickness surrounding a connector through-bore sized to receive a tool shaft, wherein the connector through-bore extends along the longitudinal axis from a connector proximal portion having a connector proximal open end to a connector distal portion having a connector distal open end;
   c) at least one slot extending through the connector sidewall from an outer connector surface to the connector through-bore thereof, wherein the slot has an angled surface extending from the connector inner surface proximally and outwardly with respect to the longitudinal axis through the connector sidewall thickness;
   d) a sleeve positioned between the housing and the connector, the sleeve comprising a sleeve sidewall having a sleeve thickness extending from a sleeve outer surface to a sleeve inner surface defining a sleeve through-bore extending along the longitudinal axis from a sleeve proximal portion having a sleeve proximal open end to a sleeve distal portion having a sleeve distal open end, wherein the sleeve is supported on an outer surface of the connector sidewall in an axially movable relationship therewith and wherein the sleeve distal portion has a cut-out comprising a frusto-conically shaped surface extending distally and outwardly with respect to the longitudinal axis from the sleeve inner surface part-way through the sleeve thickness to a ledge extending to the sleeve distal open end;
   e) a spring positioned circumferentially around the connector within the housing, wherein the spring biases between the housing proximal portion and the sleeve proximal portion; and
   f) at least one locking ball received within the at least one slot, the ball being sized to extend only part-way into the connector through-bore from the slot,
   g) wherein proximal axial movement of a tool shaft into the connector through-bore causes the at least one bail to move proximally and outwardly along the angled surface of the connector slot and into the sleeve cut-out as the biased sleeve moves proximally along the connector until the ball is laterally removed from the connector through-bore so that the tool shaft is receivable therein, and
   h) wherein when an annular groove in the tool shaft is aligned with the ball, the biased sleeve moves in a distal direction, which causes the ball to move laterally into the tool shaft groove until the ball is captured therein by the connector slot and against the frusto-conical surface and the ledge of the sleeve cut-out and the distal lip of the housing, and
   i) wherein the housing is then manipulatable in a proximal direction to cause the lip to contact the ball and the distal sleeve end to thereby cause the ball to move along the angled surface of the connector slot as the housing simultaneously moves the biased sleeve proximally with the ball again moving along the frusto-conical surface of the sleeve cut-out to thereby laterally remove the ball from the tool shaft groove so that the tool shaft is manipulatable in a distal direction out of the connector through-bore.

13. The connector mechanism of claim 12 wherein the angled surface of the slot is angled from about 35° to about 55° with respect to the longitudinal axis of the connector.

14. The connector mechanism of claim 12 wherein, with the ball received in the groove of the tool shaft, an edge of the connector sidewall at the slot is positioned below a centerline of the locking ball.

15. The connector mechanism of claim 12 wherein the housing has a ridge that protrudes from an outer housing surface and extends circumferentially around the housing.

16. The connector mechanism of claim 12 wherein the proximal portion of the connector is removably connectable to a surgical tool handle or a motor.

17. The connector mechanism of claim 12 being removably connectable to an orthopedic tool comprising the tool shaft.

18. The connector mechanism of claim 12 wherein, with respect to the longitudinal axis, the connector proximal portion protrudes axially beyond the housing proximal open end and the connector distal portion protrudes axially beyond the housing distal open end.

19. The connector mechanism of claim 12 wherein the lip at the distal housing portion is an annular lip.

20. A connector mechanism for a surgical tool, the mechanism comprising:
   a) a housing comprising a housing sidewall surrounding a housing through-bore extending along a longitudinal axis from a housing proximal portion defining a housing proximal open end to a housing distal portion defining a housing distal open end;
   b) a connector residing inside the housing through-bore, wherein the connector comprises a connector sidewall having a connector sidewall thickness surrounding a connector through-bore sized to receive a tool shaft, wherein the connector through-bore extends along the longitudinal axis from a connector proximal portion having a connector proximal open end to a connector distal portion having a connector distal open end;
   c) at least one slot extending through the connector sidewall from an outer connector surface to the connector through-bore thereof, wherein the slot has an angled surface extending from the connector inner surface proximally and outwardly with respect to the longitudinal axis through the connector sidewall thickness;
   d) a sleeve positioned between the housing and the connector, the sleeve comprising a sleeve sidewall having a sleeve thickness extending from a sleeve outer surface to a sleeve inner surface defining a sleeve through-bore extending along the longitudinal axis from a sleeve proximal portion having a sleeve proximal open end to a sleeve distal portion having a sleeve distal open end, wherein the sleeve is supported on an outer surface of the connector sidewall in an axially movable relationship therewith and wherein the sleeve distal portion has a cut-out comprising a frusto-conically shaped surface extending distally and outwardly with respect to the longitudinal, axis from the sleeve inner surface at least part-way through the sleeve thickness to the sleeve distal open end;

e) a spring positioned circumferentially around the connector within the housing, wherein the spring biases between the housing proximal portion and the sleeve proximal portion; and f) at least one locking ball received within the at least one slot, the ball being sized to extend only part-way into the connector through-bore from the slot, g) wherein proximal axial movement of a tool shaft into the connector through-bore causes the at least one ball to move proximally and outwardly along the angled surface of the connector slot and into the sleeve cut-out as the biased sleeve moves proximally along the connector until the ball is laterally removed from the connector through-bore so that the tool shaft is receivable therein, and h) wherein when an annular groove in the tool shaft is aligned with the ball, the biased sleeve moves in a distal direction, which causes the ball to Move laterally into the tool shaft groove until the ball is captured therein by the connector slot and against the frusta-conical surface of the sleeve cut-out and the housing distal portion, and i) wherein the housing is then manipulatable in a proximal direction to cause the housing distal portion to contact the ball and the distal sleeve end to thereby cause the ball to move along the angled surface of the connector slot as the housing simultaneously moves the biased sleeve proximally with the ball again moving along the frusto-conical surface of the sleeve cut-out to thereby laterally remove the ball from the tool shaft groove so that the tool shaft is manipulatable in a distal direction out of the connector through-bore.

* * * * *

UNITED STATES PATENT AND TRADEMARK OFFICE
CERTIFICATE OF CORRECTION

PATENT NO. : 8,844,942 B1
APPLICATION NO. : 13/169742
DATED : September 30, 2014
INVENTOR(S) : Steve Landowski and Kevin K. Marchant It is certified that error appears in the above-identified patent and that said Letters Patent is hereby corrected as shown below:

In the claims

Column 10, line 65 after the word "longitudinal" delete the ","

Column 11, line 18 delete "Move" and insert --move--

Signed and Sealed this
Twenty-sixth Day of April, 2016

Michelle K. Lee
*Director of the United States Patent and Trademark Office*